US012379297B2

(12) United States Patent
Suzuki et al.

(10) Patent No.: US 12,379,297 B2
(45) Date of Patent: Aug. 5, 2025

(54) GAS MEASUREMENT DEVICE AND GAS MEASUREMENT METHOD

(71) Applicants: SINTOKOGIO, LTD., Nagoya (JP); National University Corporation TOYOHASHI UNIVERSITY OF TECHNOLOGY, Toyohashi (JP)

(72) Inventors: Yoshihisa Suzuki, Toyokawa (JP); Toshihiko Noda, Toyohashi (JP); Kazuaki Sawada, Toyohashi (JP)

(73) Assignees: SINTOKOGIO, LTD., Nagoya (JP); National University Corporation TOYOHASHI UNIVERSITY OF TECHNOLOGY, Toyohashi (JP)

( * ) Notice: Subject to any disclaimer, the term of this patent is extended or adjusted under 35 U.S.C. 154(b) by 247 days.

(21) Appl. No.: 17/802,244

(22) PCT Filed: Feb. 3, 2021

(86) PCT No.: PCT/JP2021/003960
§ 371 (c)(1),
(2) Date: Aug. 25, 2022

(87) PCT Pub. No.: WO2021/176936
PCT Pub. Date: Sep. 10, 2021

(65) Prior Publication Data

US 2023/0078944 A1 Mar. 16, 2023

(30) Foreign Application Priority Data

Mar. 5, 2020 (JP) ................................ 2020-038056

(51) Int. Cl.
*G01N 15/06* (2024.01)
*B01D 46/10* (2006.01)

(52) U.S. Cl.
CPC ......... *G01N 15/0656* (2013.01); *B01D 46/10* (2013.01); *B01D 2275/203* (2013.01);
(Continued)

(58) Field of Classification Search
CPC ..... G01N 1/2205; G01N 33/009; B01D 46/10
See application file for complete search history.

(56) References Cited

U.S. PATENT DOCUMENTS 5,092,980 A * 3/1992 Maurer ................ G01N 27/404 204/415
7,993,606 B2 * 8/2011 Trentacosta ........... B01D 69/02 2/457

(Continued)

FOREIGN PATENT DOCUMENTS

CN 206772932 U 12/2017
JP H09-033467 A 2/1997
JP 2014-173947 A 9/2014

OTHER PUBLICATIONS

Hidehiko et al., MOSFET-Type Gas Sensor, Feb. 1997, FIT Machine Translation (Year: 1997).*

(Continued)

*Primary Examiner* — Erika J. Villaluna
(74) *Attorney, Agent, or Firm* — Faegre Drinker Biddle & Reath LLP

(57) ABSTRACT

The gas measurement device includes a filter having a plurality of openings, each opening being variable in size, an adjustment mechanism configured to vary size of the plurality of openings, a first gas sensor configured to detect gas molecules passing through an opening of the filter and output a first measurement value corresponding to the detected gas molecules, and a second gas sensor configured to detect the gas molecules passing through the opening of the filter, output a second measurement value corresponding
(Continued)

to the detected gas molecules, and detect gas molecules of a gas species different from the gas molecules detected by the second gas sensor.

6 Claims, 5 Drawing Sheets

(52) U.S. Cl.
CPC .................. *B01D 2275/302* (2013.01); *G01N 2015/0662* (2013.01)

(56) References Cited

U.S. PATENT DOCUMENTS

| | | | | |
|---|---|---|---|---|
| 9,989,492 | B1 * | 6/2018 | Cheng ................ | G01N 27/4045 |
| 2001/0045119 | A1 | 11/2001 | Warburton | |
| 2009/0314696 | A1 | 12/2009 | Trentacosta et al. | |
| 2017/0269025 | A1 | 9/2017 | Wolf et al. | |
| 2019/0145930 | A1 | 5/2019 | Murthy et al. | |
| 2021/0285912 | A1 * | 9/2021 | Cheng ................ | G01N 27/4065 |

OTHER PUBLICATIONS

Extended European Search Report issued Feb. 6, 2024 in Application No. 21765487.0.
International Preliminary Report on Patentability mailed Sep. 15, 2022 for PCT/JP2021/003960.

* cited by examiner (A)

(B)

GAS MEASUREMENT DEVICE AND GAS MEASUREMENT METHOD

TECHNICAL FIELD

The present disclosure relates to a gas measurement device and a gas measurement method.

BACKGROUND ART

Patent Document 1 discloses a gas sensor. The gas sensor includes a slit for gas introduction formed of a piezoelectric material. The diameter of the slit varies in accordance with the voltage applied to the slit. The gas sensor varies the diameter of the slit and selectively detects only gas molecules of a gas to be measured.

CITATION LIST

Patent Document

Patent Document 1: Japanese Unexamined Patent Publication No. H09-33467

The gas to be measured may contain gas molecules having different compositions and substantially the same size. In such a case, the gas sensor described in Patent Document 1 cannot sieve gas molecules having different compositions with the filter. For this reason, the gas sensor described in Patent Document 1 may not be able to accurately measure the component or quantity of the gas to be measured. The present disclosure provides a gas measurement device and a gas measurement method capable of improving gas measurement accuracy.

Solution to Problem

A gas measurement device according to one aspect of the present disclosure includes a filter, an adjustment mechanism, a first gas sensor, and a second gas sensor. The filter has a plurality of openings each of which is variable in size. The adjustment mechanism varies the size of the plurality of openings. The first gas sensor detects gas molecules passing through the opening of the filter and outputs a first measurement value corresponding to the detected gas molecules. The second gas sensor can detect gas molecules passing through the opening of the filter, output a second measurement value corresponding to the detected gas molecules, and detect gas molecules of a gas species different from the gas molecules detected by the first gas sensor.

The gas to be measured by this gas measurement device is sieved into the openings based on the size of the gas molecules. The gas molecules passing through the opening are detected by a first gas sensor and the second gas sensor capable of detecting gas molecules different from the first gas sensor. A first measurement value corresponding to the detected gas molecules is outputted by the first gas sensor. A second measurement value different from the first measurement value is outputted by the second gas sensor in response to the detected gas molecules. As described above, since the gas measurement device includes the plurality of sensors having different gas detection performances downstream of the filter, it is possible to improve gas measurement accuracy compared to a gas measurement device including a gas sensor having a single type of gas detection performance downstream of the filter.

In one embodiment, the filter may include a first member and a second member disposed so as to overlap the first member. The plurality of openings is comprised of the first member and the second member. The first member and the second member are movable relative to each other. The adjustment mechanism may move at least one of the first member and the second member to vary the size of the plurality of openings. In this case, the gas measurement device can vary the size of the plurality of openings only by moving at least one of the first member and the second member. In particular, when both of the first member and the second member are moved, the way of adjusting the size of the opening is various as compared with the case where only one of them is moved.

In one embodiment, the filter may be formed of a plate-shaped elastic member, and the adjustment mechanism may elastically deform the filter to vary the size of the plurality of openings. In this case, the gas measurement device can vary the size of the plurality of openings by the magnitude of the thrust of the adjustment mechanism.

In one embodiment, the filter is formed of a porous material expanding or contracting depending on temperature, and the adjustment mechanism may vary the temperature of the filter to vary the size of the plurality of openings. In this case, the gas measurement device can vary the size of the plurality of openings with temperature.

In one embodiment, the gas measurement device may include a signal generation unit configured to output a synchronous signal, a control unit, an acquirement unit, and an output unit. The control unit controls the adjustment mechanism based on a control signal for determining the sizes of the plurality of openings and the synchronous signal. The acquirement unit acquires the first measurement value and the second measurement value based on the synchronous signal. The output unit outputs both the first measurement value and the second measurement value, and the control signal in association with each other. In this case, the gas measurement device may output both the first measurement value and the second measurement value, and the control signal in association with each other using the synchronous signal.

In one embodiment, the gas measurement device may include a determination unit that determines a gas species. The determination unit determines the gas species based on a pre-acquired relationship, the first measurement value, the second measurement value, and the control signal output by the output unit. The pre-acquired relationship is a relationship between the gas species, the first measurement value, the second measurement value, and the control signal. In this case, the gas measurement device can determine the gas species of the mixed gas including gas molecules of different sizes.

A gas measurement method according to another aspect of the present disclosure includes the following steps (1) to (4).

(1) varying sizes of a plurality of openings included in a filter based on a control signal for determining sizes of the plurality of openings and a synchronous signal.

(2) detecting gas molecules passing through the opening by a first gas sensor and a second gas sensor capable of detecting the gas molecules different from the first gas sensor.

(3) acquiring a first measurement value output by the first gas sensor and a second measurement value output by the second gas sensor in synchronization with the synchronous signal.

(4) determining a gas species based on a pre-acquired relationship, the acquired first measurement value, the acquired second measurement value, and the acquired control signal, wherein the pre-acquired relationship is a relationship between the gas species, the first measurement value, the second measurement value, and the control signal.

According to this gas measurement method, the measurement accuracy of gas can be improved.

Advantageous Effects of Invention

According to the gas measurement device and the gas measurement method of the present disclosure, it is possible to improve measurement accuracy of gas.

Figure 2:
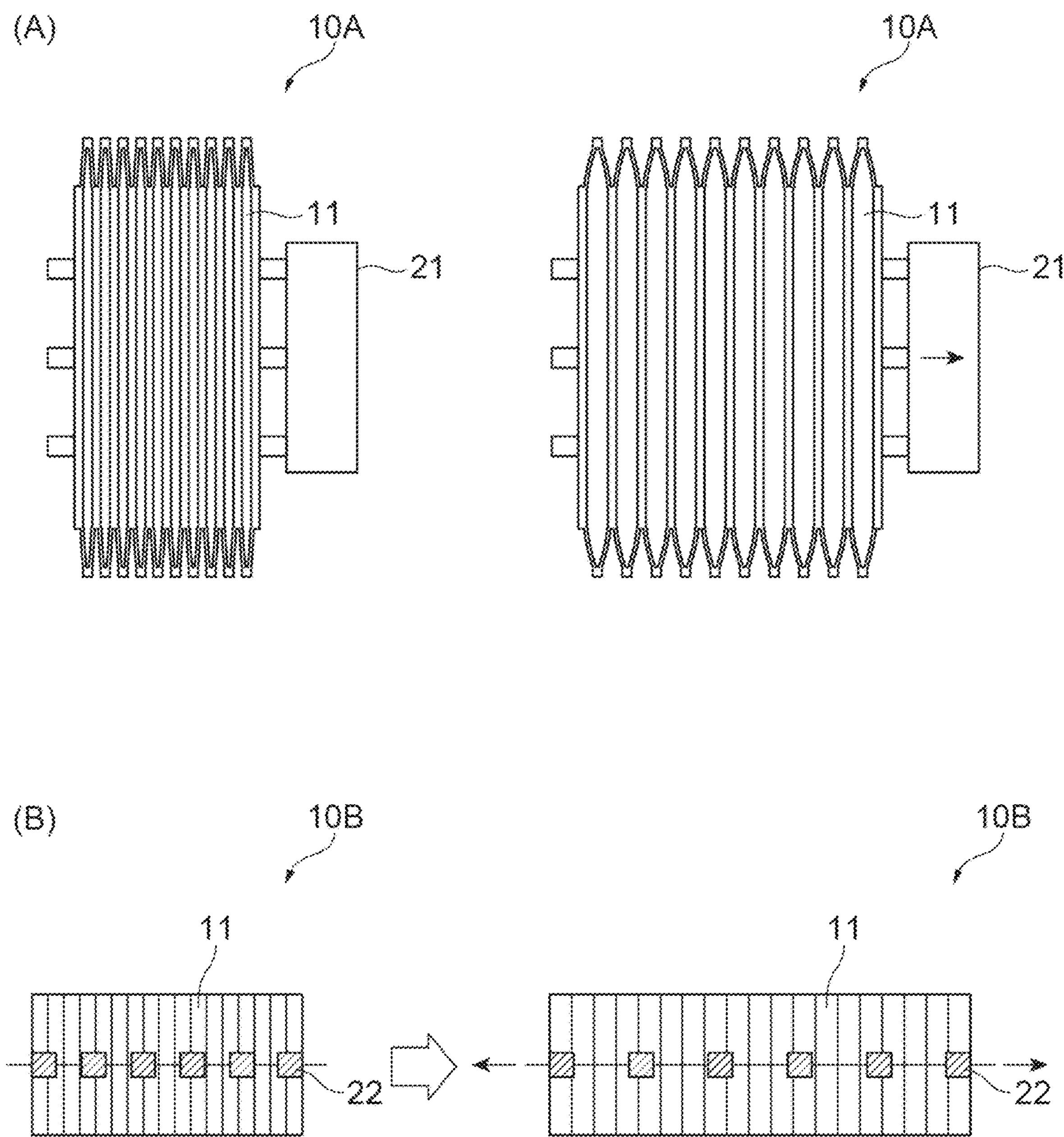

(A) of FIG. 2 is a plan view showing a stripe filter as an example of a filter. (B) of FIG. 2 is a plan view showing a porous material filter as an example of a filter.

Figure 3:
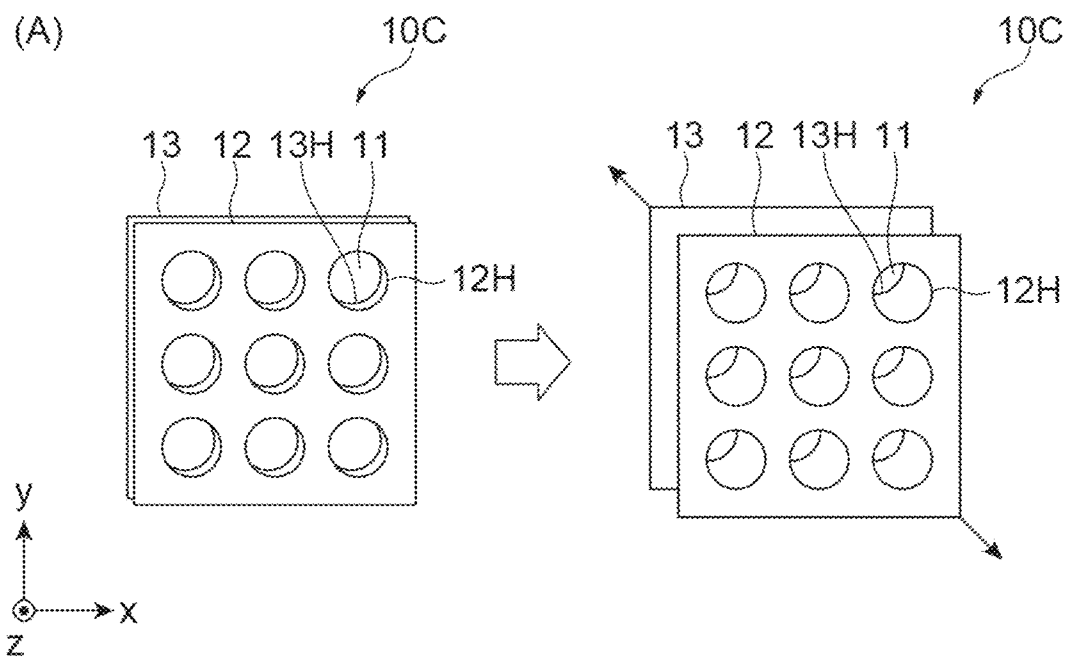
Figure 3:
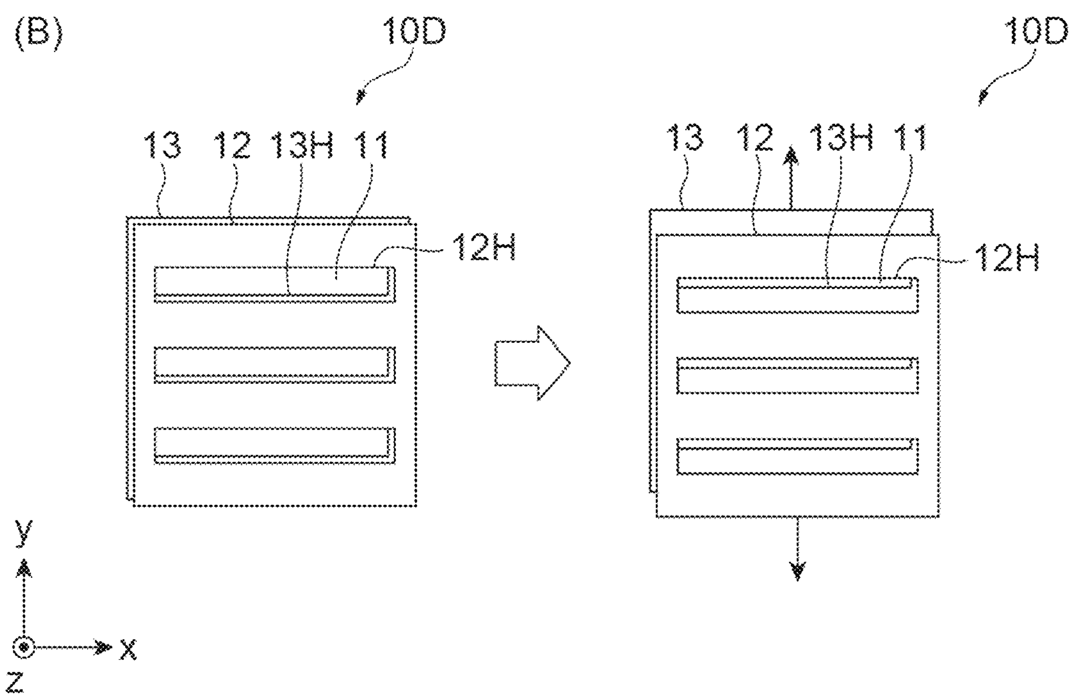

(A) of FIG. 3 is a plan view showing a mesh filter as an example of a filter. (B) of FIG. 3 is a plan view showing a slit filter as an example of a filter.

Figure 4:
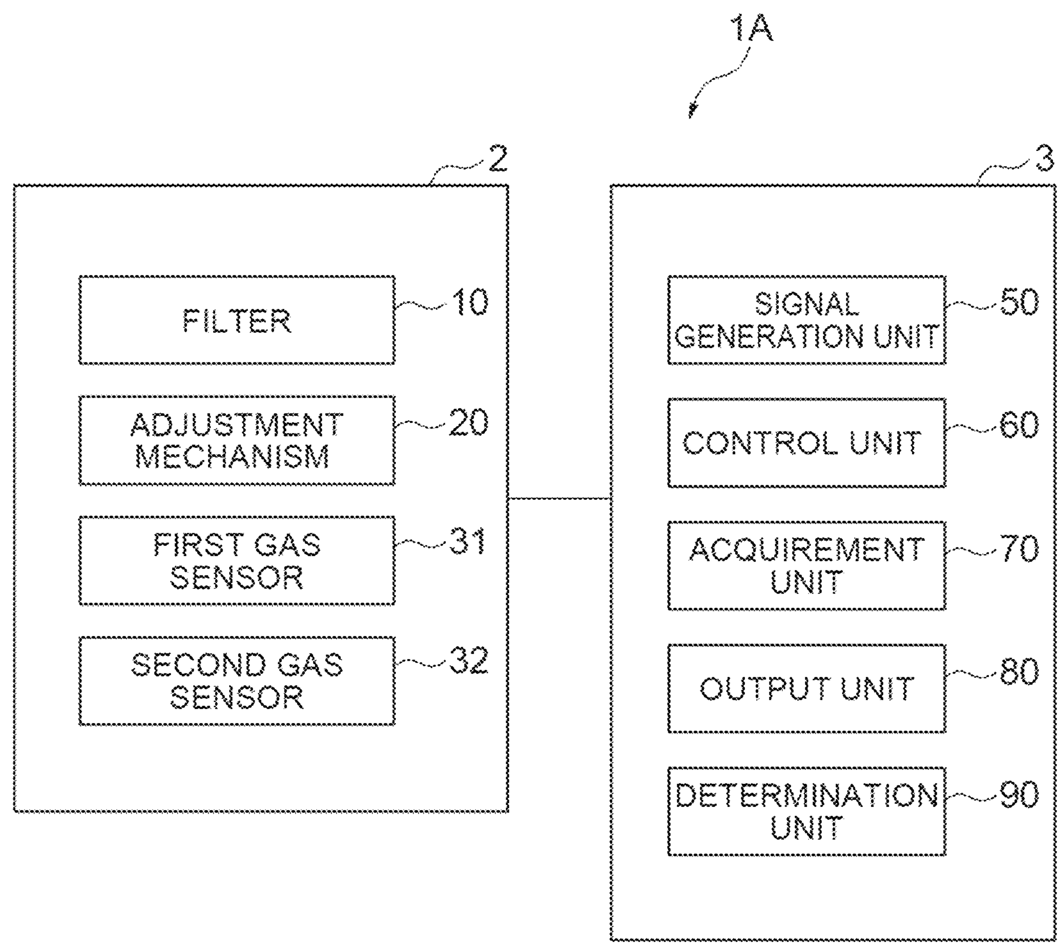
Figure 4:
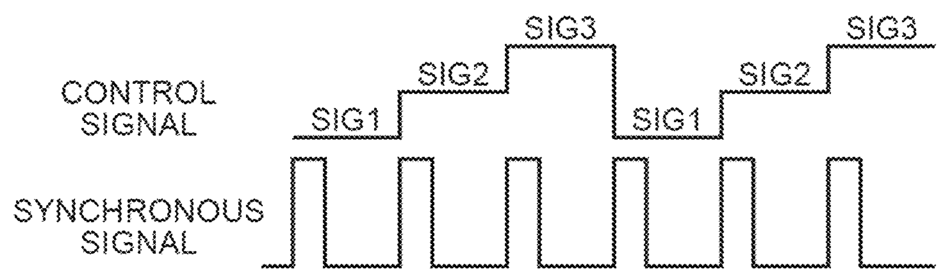

(A) of FIG. 4 is a block diagram illustrating an example of the gas measurement device according to the embodiment. (B) of FIG. 4 is an example of the control signal and the synchronous signal.

Figure 5:
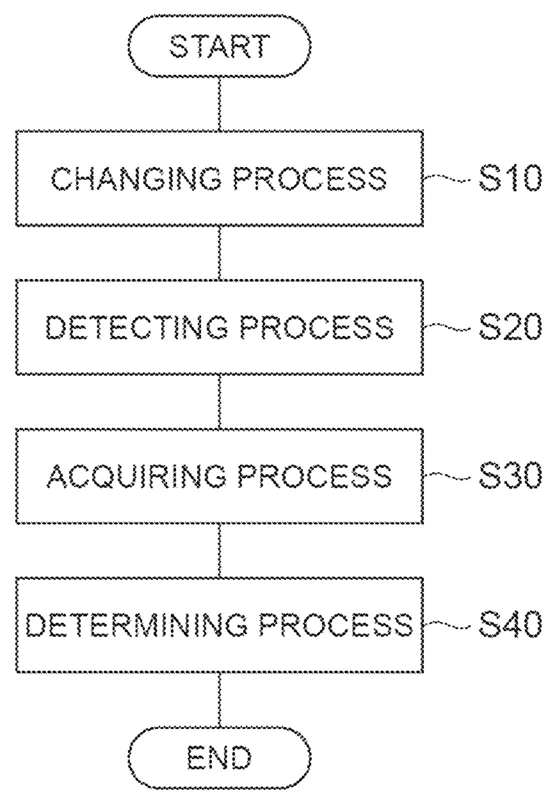

FIG. 5 is a flowchart illustrating an example of a gas measurement method according to an embodiment;

DESCRIPTION OF EMBODIMENTS

An embodiment of the present disclosure is described below with reference to the drawings. In the description below, the same or equivalent elements are denoted by the same reference characters, and overlapping description is not repeated. Dimension ratios of the drawings do not necessarily match with those described. Terms “up”, “down”, “left”, and “right” are based on the illustrated states and are for convenience.

[Configuration of Gas Measurement Device]

Figure 1:
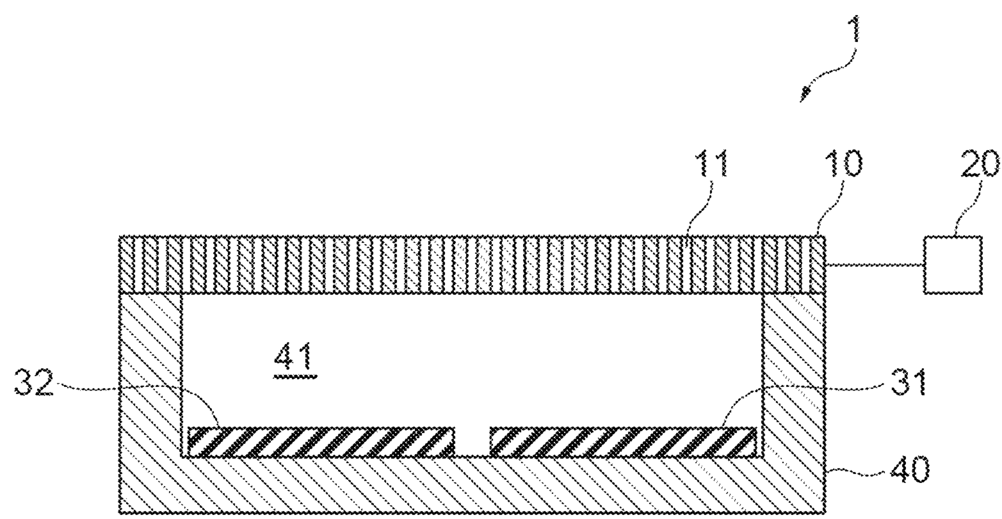
FIG. 1 is a cross-sectional view illustrating an example of a gas measurement device according to an embodiment.

FIG. 1 is a cross-sectional view illustrating an example of a gas measurement device 1 according to an embodiment. The gas measurement device 1 shown in FIG. 1 is a device for measuring gas components. The gas measurement device 1 may be provided as an electric circuit component. As an example, the gas measurement device 1 is a micro electro mechanical systems (MEMS) device. The gas measurement device 1 includes a filter 10, an adjustment mechanism 20, a base member 40, a first gas sensor 31, and a second gas sensor 32.

The base member 40 defines a space therein. The base member 40 is formed of a gas-impermeable material. The base member 40 is open at its upper portion and has an opening communicating with the space. The filter 10 is disposed so as to close the opening in the upper portion of the base member 40. The filter 10 is a substantially plate-shaped member. The filter 10 and the base member 40 are joined so that there is no gap through which gas passes. Thus, the filter 10 and the base member 40 define a gas chamber 41. The first gas sensor 31 and the second gas sensor 32 are disposed in the gas chamber 41. The first gas sensor 31 and the second gas sensor 32 detect gas molecules passing through the filter 10 and supplied to the gas chamber 41.

The filter 10 has a plurality of openings 11 each of which is variable in size. The plurality of openings 11 can be varied in size to allow predetermined gas molecules to pass therethrough. The predetermined gas molecule is a gas molecule assumed to be detected. The predetermined gas molecule is, for example, a gas molecule of hydrogen sulfide or a volatile gas. The size of the opening 11 is set larger than the size of a predetermined gas molecule. Gas molecules smaller than the opening 11 pass through the opening 11 and gas molecules larger than the opening 11 are blocked by the opening 11.

The adjustment mechanism 20 varies the size of the plurality of openings of the filter 10. The adjustment mechanism 20 may be a drive device that operates the filter 10 or may be a temperature adjustment device. The adjustment mechanism 20 is selected based on the operating principle of the filter 10. Details of the adjustment mechanism 20 will be described later.

[Details of Configuration of Filter]

(A) of FIG. 2 is a plan view showing the stripe filter 10A as an example of the filter 10. As shown in (A) of FIG. 2, the stripe filter 10A is a plate-shaped member having a plurality of openings 11 and is about several micrometers thick. An example of stripe filter 10A is formed of silicon. The stripe filter 10A is an elastic member. As an example, the stripe filter 10A is formed in a bellows shape. The bellows-shaped stripe filter 10A is formed by arranging a plurality of band members in a direction orthogonal to axial lines of the band members and connecting end portions of adjacent band members. The stripe filter 10A is elastically deformed in the direction in which the plurality of openings 11 are juxtaposed. The MEMS actuator 21 (an example of the adjustment mechanism 20) is connected to the stripe filter 10A so that force is applied in the direction in which the plurality of openings 11 are arranged in parallel. The MEMS actuator 21 is driven by an electrostatic force.

In (A) of FIG. 2, the left end of the stripe filter 10A is connected to a fixed end (not shown). The MEMS actuator 21 is connected to the right end of the stripe filter 10A. When the MEMS actuator 21 is not driven, the stripe filter 10A is in a contracted state. When the MEMS actuator 21 is driven in the right direction, the stripe filter 10A is elastically deformed in the extending direction. Note that the MEMS actuators 21 may be provided at both ends of the stripe filter 10A. When the MEMS actuator 21 is not actuated, the stripe filter 10A may be in an extended state.

The size of the openings 11 in the stripe filter 10A is varied by the MEMS actuator 21. The size of the opening 11 decreases as the stripe filter 10A contracts. The size of the opening 11 increases as the stripe filter 10A expands.

The size of the opening 11 is determined by the amount of deformation of the stripe filter 10A. The amount of deformation of the stripe filter 10A is determined by the thrust of the MEMS actuator 21. The thrust of the MEMS actuator 21 is determined according to the magnitude of the current or voltage applied to the MEMS actuator 21. Therefore, the size of the opening 11 can be varied to a predetermined size by the magnitude of the current or voltage applied to the MEMS actuator 21.

Other Examples of Configuration of Filter (B) of FIG. 2 is a cross-sectional view showing the porous-material filter 10B as an example of the filter 10. The porous-material filter 10B is formed of a porous-material that expands or contracts depending on temperature. The porous material is formed of a sintered resin or the like and has a plurality of openings 11. The porous-material filter 10B is provided with a heater 22 (an example of an adjustment mechanism) that changes the size of the plurality of openings 11 by varying the temperature of the porous-material filter 10B.

The porous-material filter 10B expands due to heat generated by the heater 22. The size of the opening 11 of the porous-material filter 10B increases in accordance with the expansion amount of the porous-material filter 10B. The expansion amount of the porous material is determined in advance depending on the physical properties of the material. The amount of heat generated by the heater 22 is determined in accordance with the magnitude of the current applied to the heater 22. Therefore, the size of the opening 11 can be varied to a predetermined size by the current applied to the heater 22.

(A) of FIG. 3 illustrates the mesh filter 10C as an example of the filter 10. An X direction and a Y direction in the drawing are in-plane directions, and a Z direction is a vertical direction. The X direction, the Y direction, and the Z direction are axis directions orthogonal to each other in an orthogonal coordinate system of a three-dimensional space. The mesh filter 10C includes a first member 12 configured to be movable in parallel to the XY plane and a second member 13 disposed to overlap the first member 12 in the Z-axis direction. The first member 12 includes a first member hole portion 12H, and the second member 13 includes a second member hole portion 13H. The mesh filter 10C forms an opening 11 by overlapping of the first member hole part 12H and the second member hole part 13H. The mesh filter 10C varies the size of the opening 11 by relatively moving the first member 12 and the second member 13 in parallel with the XY plane. The MEMS actuators 21 (not shown) that relatively move the first member 12 and the second member 13 are connected to end portions of the mesh filter 10C.

The first member 12 and the second member 13 are, for example, thin plate members of silicon processed by etching or the like. The first member hole portion 12H and the second member hole portion 13H are circular holes penetrating through the plate member in the Z direction provided at predetermined intervals. The first member hole portion 12H overlaps the second member hole portion 13H to form an opening 11 through which the first member 12 and the second member 13 communicate with each other. The sizes of the plurality of openings 11 are varied at a time by relative movement of the first member 12 and the second member 13.

When the size of the opening 11 becomes maximum, the coordinates on the XY plane of the first member hole portion 12H and the second member hole portion 13H overlap. In this case, the size of gas molecules passing through the opening 11 is the same as the size of gas molecules passing through the first member hole portion 12H or the second member hole portion 13H. When the first member 12 and the second member 13 move relative to each other from this state, the size of the opening 11 decreases. The gas molecules larger than the size of the opening 11 are blocked. When the first member 12 and the second member 13 further move relative to each other from this state, the opening 11 is closed because the first member hole portion 12H and the second member hole portion 13H do not overlap each other. In this manner, the size of the opening 11 is varied by the relative movement of the first member 12 and the second member 13. Here, "relative movement between the first member 12 and the second member 13" is a concept including both a case where either the first member 12 or the second member 13 is moved and a case where both the first member 12 and the second member 13 are moved.

The first member hole portion 12H and the second member hole portion 13H may have a slit shape. (B) of FIG. 3 is a slit filter 10D as an example of the filter 10. The slit filter 10D varies the size of the opening 11 by moving the first member 12 and the second member 13 in the Y-axis direction.

[Details of Gas Sensor]

The second gas sensor 32 is configured to be capable of mainly detecting gas molecules of a type different from the gas molecules detected by the first gas sensor 31. As a gas detection method of the first gas sensor 31 and the second gas sensor 32, a semiconductor method is used as an example. The gas molecules that can be detected by the gas sensor are determined by the sensitivity corresponding to the type of gas molecule. The sensitivity of a semiconductor type sensor varies depending on the characteristics of a semiconductor used and the temperature of the semiconductor. Therefore, as the second gas sensor 32, a semiconductor having characteristics different from those of the first gas sensor 31 or a semiconductor having a temperature different from the first gas sensor 31 is used. The gas detection method of the first gas sensor 31 and the second gas sensor 32 may be an electrochemical method, a crystal oscillator method, or a surface-acoustic-wave method. Different detection methods may be used for the first gas sensor 31 and the second gas sensor 32 as long as the sensitivities corresponding to the types of gas molecules are different.

The first gas sensor 31 and the second gas sensor 32 output measured values of predetermined gas molecules passing through the opening 11. The measurement values output by the first gas sensor 31 and the second gas sensor 32 are, for example, varies in voltage accompanying varies in resistance values in the case of semiconductor type sensors. The magnitude of the sensitivity of the sensor is determined by the magnitude of the voltage vary with respect to the gas. The sensitivity of the first gas sensor 31 is different from that of the second gas sensor 32. Therefore, the first measurement value output by the first gas sensor 31 is different from the second measurement value output by the second gas sensor 32 in the magnitude of change in voltage corresponding to the type of gas molecules. The gas measurement device 1 can measure gas components contained in the detected gas based on the predetermined sensitivity of the gas sensor, the first measurement value, and the second measurement value.

[Control Circuit of Gas Measurement Device]

(A) of FIG. 4 is a block diagram illustrating an example of the gas measurement device 1A according to the embodiment. The gas measurement device 1A includes a measuring unit 2 (an example of a gas measurement device) and a circuit unit 3. The circuit unit 3 includes a signal generation unit 50, a control unit 60, an acquirement unit 70, an output unit 80, and a determination unit 90. The circuit unit 3 may be formed of, for example, an electric circuit. The circuit unit 3 may be configured by, for example, a general-purpose computer including an arithmetic device such as a central processing unit (CPU), a storage device such as a read only memory (ROM), a random access memory (RAM), and a hard disk drive (HDD), and a communication device.

The signal generation unit 50 outputs a control signal and a synchronous signal to the control unit 60 and the acquirement unit 70. The control signal is a signal that determines the size of the plurality of openings. The synchronous signal is a signal for synchronizing the control unit 60 and the acquirement unit 70. The control unit 60 outputs a signal for controlling the size of the opening 11 to the adjustment mechanism 20 based on the control signal and the synchronous signal. (B) of FIG. 4 is an example of the control signal and the synchronous signal. In (B) of FIG. 4, the control signal is a signal indicating the states (shapes) of three kinds of openings of SIG1, SIG2, and SIG3. The synchronous signal is a rectangular wave based on an oscillator such as a crystal oscillator. The control unit 60 operates the adjustment mechanism 20 based on the synchronous signal so as to achieve the state of the opening indicated by the control signal. The acquirement unit 70 acquires the first measurement value and the second measurement value based on the synchronous signal.

When the rectangular wave of the synchronous signal is received a predetermined number of times, the control unit 60 outputs the signal to the adjustment mechanism 20. The control unit 60 outputs a control signal having a waveform corresponding to the size of the opening 11. As an example, the control signal that changes in three stages in (B) of FIG. 4 controls the size of the opening 11 in three stages. The size of the opening 11 may be steplessly controlled. In this case, the control signal indicates a triangular wave or a sine wave.

The acquirement unit 70 acquires the first measurement value and the second measurement value when the rectangular wave of the synchronous signal is received a predetermined number of times. Therefore, the acquirement unit 70 can acquire the first measurement value and the second measurement value corresponding to the change in the size of the opening 11 caused by the control signal. The predetermined number of times the acquirement unit 70 receives the first measurement value and the rectangular wave when acquiring the second measurement value may be equal to or greater than the number of times the control unit 60 receives the rectangular wave when outputting the control signal. By setting the timing at which the acquirement unit 70 acquires the first measurement value and the second measurement value to be later than the timing at which the control unit 60 outputs the control signal, the acquirement unit 70 can acquire the first measurement value and the second measurement value when the number of gas molecules passing through the opening 11 becomes large after the size of the opening 11 changes.

The output unit 80 outputs the control signal and both the first measurement value and the second measurement value acquired from the acquirement unit 70 in association with each other.

The determination unit 90 determines the gas species based on a pre-acquired relationship, the first measurement value, the second measurement value, and the control signal output by the output unit. The pre-acquired relationship is a relationship between the gas species, the first measurement value, the second measurement value, and the control signal. A combination of the gas species, the first measurement value, the second measurement value, and the control signal are acquired in advance and stored as, for example, a gas characteristic table. The determination unit 90 determines the gas species with reference to the gas characteristic table based on the combination output by the output unit 80.

[Operation of Gas Measurement Device]

FIG. 5 is a flowchart illustrating an example of the gas measurement method according to an embodiment. The steps of the flow chart shown in FIG. 5 illustrate the operation of the gas measurement device 1A. As an example, the gas to be detected is a mixed gas containing methane ($CH_4$), carbon monoxide (CO), and toluene ($C_7H_8$). The first gas sensor 31 and the second gas sensor 32 include a sensor (an example of the first gas sensor 31) having high sensitivity to carbon monoxide and a sensor (an example of the second gas sensor 32) having high sensitivity to hydrocarbons.

As shown in FIG. 5, first, the size of the plurality of openings 11 of the filter 10 is varied to a size that allows a predetermined gas to pass through by the adjustment mechanism 20 that operates based on the synchronous signal (step S10). Among the gases contained in the mixed gas, the gas molecules of toluene ($C_7H_8$) have the largest diameters. When the size of the opening 11 is varied to a size that blocks toluene ($C_7H_8$) (step S10), the first gas sensor 31 and the second gas sensor 32 detect a predetermined mixed gas containing methane ($CH_4$) and carbon monoxide (CO) (step S20).

Next, the acquirement unit 70 acquires the first measurement value output by the first gas sensor 31 and the second measurement value output by the second gas sensor 32 based on the synchronous signal (step S30). In this case, the measurement value of the first gas sensor 31 indicates that carbon monoxide (CO) is contained in the predetermined mixed gas. The measurement value of the second gas sensor 32 indicates that hydrocarbon is contained in the predetermined mixed gas.

The determination unit 90 determines the gas species based on the gas characteristic table, the first measurement value, the second measurement value, and the control signal (step S40). The first measurement value, the second measurement value, and the control signal are acquired by the acquirement unit 70. From the pre-acquired relationship between the size of the opening 11 indicated by the control signal and the second measurement value, it is determined that the second measurement value acquired by the acquirement unit 70 indicates methane ($CH_4$).

Next, when the size of the opening 11 is changed to a size that allows toluene ($C_7H_8$) to pass therethrough (step S10), the first gas sensor 31 and the second gas sensor 32 detect a predetermined mixed gas containing methane ($CH_4$), carbon monoxide (CO), and toluene ($C_7H_8$) (step S20). In this case, the measurement value of the second gas sensor 32 acquired by the acquirement unit 70 indicates that the hydrocarbons include methane ($CH_4$) and other hydrocarbons (step S30). The determination unit 90 determines that the other hydrocarbon is toluene ($C_7H_8$) based on the gas characteristic table and the control signal (step S40).

Summary of Embodiment

In the gas measurement device 1, the gas to be measured is screened into the opening 11 on the basis of the size of the gas molecules. The gas molecules passing through the opening 11 are detected by a first gas sensor 31 and a first gas sensor 32 capable of detecting gas molecules different from the second gas sensor 31. First measurement values corresponding to the detected gas molecules are output by the first gas sensor 31. The second gas sensor 32 outputs a first measurement value different from the second measurement value in accordance with the detected gas molecules. As described above, since the gas measurement device 1 includes a plurality of sensors having different gas detection performances downstream of the filter 10, gas measurement accuracy can be improved compared to a gas measurement device including a gas sensor having a single type of gas detection performance downstream of the filter 10.

In the gas measurement device 1, the size of the plurality of openings 11 can be varied by the magnitude of the thrust of the MEMS actuator 21.

In the gas measurement device 1, the size of the plurality of openings 11 can be varied by the output of the heater 22. The gas measurement device 1 can vary the size of the opening 11 only by adjusting the temperature.

The gas measurement device 1 can vary the sizes of the plurality of openings 11 at once. This gas measurement device can sieve out gas molecules with high accuracy compared to a case where the filter 10 is constituted by one member. Further, the size of the plurality of openings 11 can be varied by relatively moving the first member 12 and the second member 13. Either one of the first member 12 or the second member 13 may be moved, or both the first member 12 and the second member 13 may be moved. When both the first member 12 and the second member 13 are moved, the gas measurement device can vary the size of the opening 11 in a wider range than when only one of the first member 12 and the second member 13 is moved.

The gas measurement device 1 and the gas measurement method can synchronize the control signal and the first measurement value and the second measurement value with the size of the opening 11 in a synchronized manner. The gas measurement device 1 and the gas measurement method can output the first measurement value and the second measurement value in association with the control signal using the synchronous signal. The gas measurement device 1 and the gas measurement method can determine gas species contained in a mixed gas containing gas molecules of different sizes.

[Modification]

While various exemplary embodiments have been described above, various omissions, substitutions and changes may be made without being limited to the exemplary embodiments described above.

The filter 10, the first gas sensor 31, and the second gas sensor 32 may be separately formed and then combined. The filter 10, the first gas sensor 31, and the second gas sensor 32 may be integrally manufactured.

The signal generation unit 50 may be integrated with the control unit 60. The acquirement unit 70 may be integrated with the output unit 80. The output unit 80 may be integrated with the determination unit 90.

The gas measurement device 1 may be configured not to include the base member 40 and the gas chamber 41. In this case, the gas measurement device 1 is configured such that the filter 10 adheres to the first gas sensor 31 and the second gas sensor 32. The gas measurement device 1 may include M types of gas sensors (M is an integer of 2 or more). When M is 3 or more, the M types of gas sensors may include the same type of sensor. The size of the opening 11 may be controlled in N stages (N is an integer of 2 or more). In this case, the gas measurement device 1 can measure the gas in a combination of M×N types at maximum.

In (A) and (B) of FIGS. 3, one of the first member 12 and the second member 13 may be fixed. The size of the first member hole portion 12H may not be the same. The size of the first member hole portion 12H may not be the same as that of the second member hole portion 13H. The intervals of the first member hole portions 12H may not be equal intervals. The first member 12 and the second member 13 may be moved relative to each other in a rotational direction about the Z-axis. The second member 13 may be a stripe filter 10A. The gas measurement device 1A may be configured not to include the determination unit 90. In this case, the output unit 80 of the gas measurement device 1A outputs the first measurement value, the second measurement value, and the control signal to the outside. The gas measurement device 1A may acquire the first measurement value and the relationship between the second measurement value and the control signal in advance by simulation. In this case, the size of the opening 11 and the sizes of various gas molecules are obtained by calculation. The first measurement and the relationship between the second measurement and the control signal may be calibrated with known gases. In this case, the relationship between the control signal and the size of the opening 11, the output characteristic of the first gas sensor 31, and the output characteristic of the second gas sensor 32 are calibrated based on the known gas in which the gas species and the size of the gas molecules are specified.

REFERENCE SIGNS LIST

1, 1A . . . gas measurement device, 2 . . . measurement unit, 3 . . . circuit unit, 10 . . . filter, 10A . . . stripe filter, 10B . . . porous-material filter, 10C . . . mesh filter, 10D . . . slit filter, 11 . . . opening, 12 . . . first member, 12H . . . first member hole, 13 . . . second member, 13H . . . second member hole, 20 . . . adjusting mechanism, 21 . . . MEMS actuator, 22 . . . heater, 31 . . . first gas sensor, 32 . . . second gas sensor, 40 . . . base member, 41 . . . gas chamber, 50 . . . signal generation unit, 60 . . . control unit, 70 . . . acquirement unit, 80 output unit, 90 . . . determination unit.

The invention claimed is:

1. A gas measurement device comprising:

a filter having a plurality of openings, each opening being variable in size;

an adjustment mechanism configured to vary size of the plurality of openings;

a first gas sensor configured to detect gas molecules passing through the plurality of openings of the filter and output a first measurement value corresponding to the detected gas molecules; and a second gas sensor configured to detect the gas molecules passing through the plurality of openings of the filter, output a second measurement value corresponding to the detected gas molecules, and detect gas molecules of a gas species different from the gas molecules detected by the first gas sensor, wherein the filter includes a first member and a second member disposed so as to overlap the first member, the first member includes first member holes, the second member includes second member holes, the plurality of openings is formed by overlapping of the first member holes and the second member holes, the first member and the second member are movable relative to each other, and the adjustment mechanism moves at least one of the first member and the second member in a direction perpendicular to an overlapping direction to vary the size of the plurality of openings.

2. The gas measurement device according to claim 1, wherein the filter is formed of a plate-shaped elastic member, and the adjustment mechanism elastically deforms the filter to vary the size of the plurality of openings.

3. The gas measurement device according to claim 1, wherein the filter is formed of a porous material expanding or contracting depending on temperature, and the adjustment mechanism varies a temperature of the filter to vary the size of the plurality of openings.

4. The gas measurement device according to claim 1, comprising:

a signal generation unit configured to output a synchronous signal;

a control unit configured to control the adjustment mechanism based on a control signal for determining sizes of the plurality of openings and the synchronous signal;

an acquirement unit configured to acquire the first measurement value and the second measurement value based on the synchronous signal; and an output unit configured to output both the first measurement value and the second measurement value, and the control signal in association with each other.

5. The gas measurement device according to claim 4, comprising a determination unit configured to determine the gas species based on a pre-acquired relationship, the first measurement value, the second measurement value, and the control signal output by the output unit, wherein the pre-acquired relationship is a relationship between the gas species, the first measurement value, the second measurement value, and the control signal.

6. A gas measurement method comprising:

varying sizes of a plurality of openings included in a filter based on a control signal for determining sizes of the plurality of openings and a synchronous signal;

detecting gas molecules passing through the plurality of openings by a first gas sensor and a second gas sensor capable of detecting the gas molecules different from the first gas sensor;

acquiring a first measurement value output by the first gas sensor and a second measurement value output by the second gas sensor in synchronization with the synchronous signal; and determining a gas species based on a pre-acquired relationship, the acquired first measurement value, the acquired second measurement value, and the acquired control signal, wherein the pre-acquired relationship is a relationship between the gas species, the first measurement value, the second measurement value, and the control signal, wherein the filter includes a first member and a second member disposed so as to overlap the first member, the first member includes first member holes, the second member includes second member holes, the plurality of openings is formed by overlapping of the first member holes and the second member holes, the first member and the second member are movable relative to each other, and the varying includes moving at least one of the first member and the second member in a direction perpendicular to an overlapping direction to vary the size of the plurality of openings.

* * * * *